(12) United States Patent
Eberhardt et al.

(45) Date of Patent: Aug. 11, 2015
(10) Patent No.: US 9,101,467 B2

(54) VALVE PROSTHESIS

(75) Inventors: Carol Eberhardt, Santa Ana, CA (US); Tomas McNatt, Irvine, CA (US); Pham Lo, Irvine, CA (US)

(73) Assignee: Medtronic Cv Luxembourg S.a.r.l., Luxembourg (LU)

( * ) Notice: Subject to any disclaimer, the term of this patent is extended or adjusted under 35 U.S.C. 154(b) by 472 days.

(21) Appl. No.: 13/435,802

(22) Filed: Mar. 30, 2012

(65) Prior Publication Data
US 2013/0261740 A1 Oct. 3, 2013

(51) Int. Cl.
*A61F 2/24* (2006.01)

(52) U.S. Cl.
CPC .............. *A61F 2/2412* (2013.01); *A61F 2/2418* (2013.01); *A61F 2220/0075* (2013.01)

(58) Field of Classification Search
CPC ....... A61F 2/2412; A61F 2/2418; A61F 2/24; A61F 2220/0075
USPC ................................................ 623/2.11, 2.37
See application file for complete search history.

(56) References Cited

U.S. PATENT DOCUMENTS

| | | | |
|---|---|---|---|
| 7,404,824 B1 | 7/2008 | Webler et al. | |
| 7,455,689 B2 | 11/2008 | Johnson | |
| 2005/0192665 A1* | 9/2005 | Spenser et al. | ............... 623/2.11 |
| 2006/0058871 A1 | 3/2006 | Zakay et al. | |
| 2007/0050021 A1* | 3/2007 | Johnson | ........................ 623/2.14 |
| 2007/0093890 A1 | 4/2007 | Eliasen et al. | |

FOREIGN PATENT DOCUMENTS

| | | |
|---|---|---|
| WO | WO03/047468 | 6/2003 |
| WO | WO2012/161786 | 11/2012 |

OTHER PUBLICATIONS

Pettenazzo et al., "Biosa Bileaflet Pericardial Valve Experimental Study in Sheep Model" Cardiovascular Pathology, 13 (2004) 207-212.
Pettenazzo, E., et al, "BIOSA bileaflet percardial valve Experimental study in sheep model," Cardiovascular Pathology 13 (2004), 207-212.

* cited by examiner

*Primary Examiner* — Tuan V Nguyen
*Assistant Examiner* — Tin Nguyen

(57) ABSTRACT

Heart valve prostheses are provided having a self-expanding frame that supports a valve body comprising a plurality of coapting leaflets. The valve body may include a first leaflet, a second leaflet, and a third leaflet, wherein the second leaflet extends between the first leaflet and the third leaflet such that the first and third leaflets are separated from each other by the second leaflet. The leaflets are constructed with four commissure points to reduce the stress and strain applied to the commissure points and to efficiently distribute forces along the leaflets and to the frame. As such, the first and second leaflets may be sewn together to form a first commissure point and a second commissure point, and the second and third leaflets may be sewn together to form a third commissure point and a fourth commissure point, with the four commissure points being sewn to the frame.

14 Claims, 5 Drawing Sheets

VALVE PROSTHESIS

BACKGROUND OF THE INVENTION

1. Field of the Invention

The present invention is related to artificial heart valves. More specifically, the present invention is directed to artificial valve prosthesis.

2. Background Art

Cardiac valves exhibit two types of pathologies: regurgitation and stenosis. Regurgitation is the more common of the two defects. Typically, either defect is treated by a surgical repair. Under certain conditions, however, the cardiac valve must be replaced. Standard approaches to valve replacement require cutting open the patient's chest and heart to access the native valve. Such procedures are traumatic to the patient, require a long recovery time, and can result in life threatening complications. Therefore, many patients requiring cardiac valve replacement are deemed to pose too high a risk for open heart surgery due to age, health, or a variety of other factors. These patient risks associated with heart valve replacement are lessened by the emerging techniques for minimally invasive valve repair, but still many of those techniques require arresting the heart and passing the blood through a heart-lung machine.

Efforts have been focused on percutaneous transluminal delivery of replacement cardiac valves to solve the problems presented by traditional open heart surgery and minimally-invasive surgical methods. In such methods, a valve prosthesis is compacted for delivery in a catheter and then advanced, for example, through an opening in the femoral artery and through the descending aorta to the heart, where the prosthesis is then deployed in the aortic valve annulus.

In view of the foregoing, it would be desirable to provide a valve prosthesis that is capable of conforming to a patient's anatomy while providing a uniform degree of rigidity and protection for critical valve components. Protection for critical valve components is essential to maintain reliability for the valve prosthesis.

BRIEF SUMMARY OF THE INVENTION

Provided herein are valve prostheses that generally include a self-expanding frame, where the valve prostheses are sutured to the self-expanding frame. Such configurations achieve numerous goals. For example, such configurations can: prevent the native leaflets from obstructing flow through the left ventricular outflow tract (LVOT); prevent the native leaflets from interacting with the prosthetic leaflets; recruit the native leaflets in minimizing perivalvular leaks; maintain proper alignment of the valve prosthesis; avoid systolic anterior mobility; and maintain valve stability by preventing migration of the valve into the atrium or ventricle. The design of the prosthesis also mimics the native valve and supports a non-round in vivo configuration, which better reproduces native valve function.

In view thereof, disclosed herein are aspects of a valve prosthesis which is generally designed to include a valve body and a self expanding frame. The valve body includes a first leaflet, a second leaflet, and a third leaflet. Adjoining leaflets are sewn together to form a first commissure point, a second commissure point, a third commissure point, and a fourth commissure point. The four commissure points are sewn to the frame.

In another exemplary embodiment, the valve prosthesis is designed to include a valve body including a first leaflet, a second leaflet, a third leaflet, and a fourth leaflet, and a self expanding frame. The first leaflet is attached to the second leaflet at a first point to form a first commissure point. The second leaflet is attached to the third leaflet at a second point to form a second commissure point. The third leaflet is attached to the fourth leaflet at a third point to form a third commissure point. The commissure points are sewn to the frame.

Disclosed herein are aspects of a method of treating a valve disorder in a patient's heart including loading a valve prosthesis onto a delivery system, advancing the delivery system and valve prosthesis through an incision into the patient's vasculature and into the patient's heart, releasing the valve prosthesis from the delivery system, and withdrawing the delivery system from the patient's heart. The valve prosthesis includes a valve body and a self-expanding frame. The valve body includes a first leaflet, a second leaflet, and a third leaflet. Adjoining leaflets are sewn together to form a first commissure point, a second commissure point, a third commissure point, and a fourth commissure point. The four commissure points are sewn to the frame.

BRIEF DESCRIPTION OF THE DRAWINGS/FIGURES

The accompanying figures, which are incorporated herein, form part of the specification and illustrate embodiments of a valve prosthesis. Together with the description, the figures further serve to explain the principles of and to enable a person skilled in the relevant art(s) to make, use, and implant the valve prosthesis described herein. In the drawings, like reference numbers indicate identical or functionally similar elements.

DETAILED DESCRIPTION OF THE INVENTION

The following detailed description of a valve prosthesis refers to the accompanying figures that illustrate exemplary embodiments. Other embodiments are possible. Modifications can be made to the embodiments described herein without departing from the spirit and scope of the present invention. Therefore, the following detailed description is not meant to be limiting.

The present invention is directed to a heart valve prosthesis having a self-expanding frame that supports a valve body. The valve prosthesis can be delivered percutaneously to the heart to replace the function of a native valve. For example, the valve prosthesis can replace a bicuspid or a tricuspid valve such as the aortic, mitral, pulmonary, or tricuspid heart valve.

In one aspect of the invention, the valve body comprises three leaflets that are fastened together at enlarged lateral end regions to form commissural joints, with the unattached edges forming the coaptation edges of the valve. The leaflets can be fastened to a skirt, which in turn can be attached to the frame. The upper ends of the commissure points define an outflow or proximal portion of the valve prosthesis. The opposite end of the valve at the skirt defines an inflow or distal portion of the valve prosthesis. The enlarged lateral end regions of the leaflets permit the material to be folded over to enhance durability of the valve and reduce stress concentration points that could lead to fatigue or tearing of the leaflets. The commissural joints are attached above the plane of the coaptation edges of the valve body to minimize the contacted delivery profile of the valve prosthesis.

Figure 2:
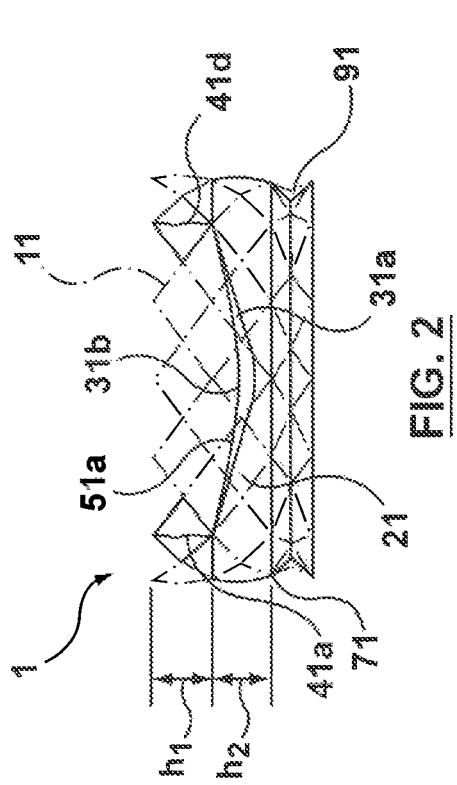
FIG. 2 is a side view of a valve prosthesis.
Figure 1:
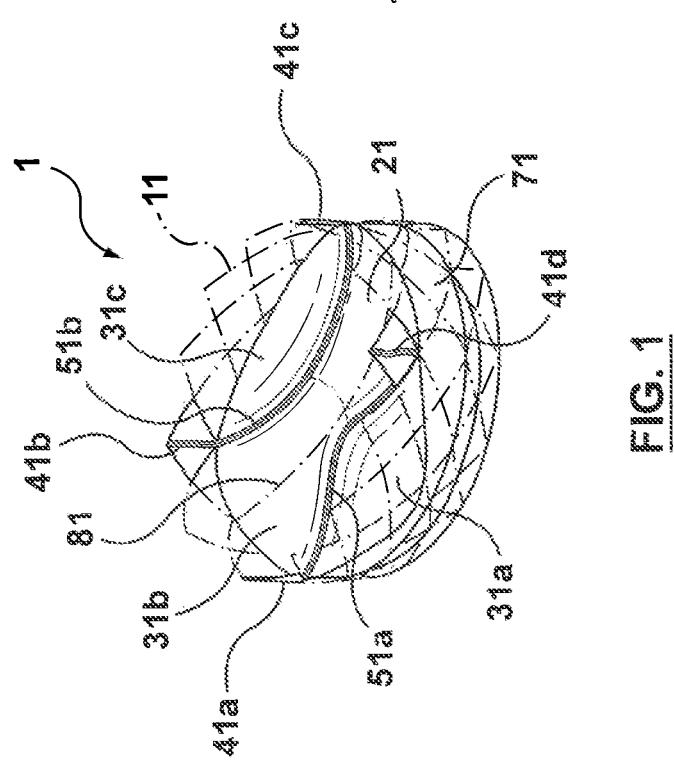
FIG. 1 is a perspective view of a valve prosthesis, in accordance with an aspect of the disclosure.

Referring to FIGS. 1 and 2, from a top view, valve prosthesis 1 includes a circular frame 11. Frame 11 can be any non-biological structure including wireforms, stents, and the like. In alternate aspects of the invention, frame 11 can be elliptical, D-shaped, or any other shape known to a person of ordinary skill in the art. From a side view, frame 11 can be tapered, cylindrical, conical, or any other shape known to a person of ordinary skill. Frame 11 can be a self-expanding structure formed by laser cutting or etching a metal alloy tube comprising, for example a shape memory material such as nickel titanium (nitinol). Alternatively, frame 11 can be a balloon expanding structure. Frame 11 can include a pattern of radial cells that make up the structure of frame 11. The cell sizes can be modified during the formation of frame 11, for example through an expansion step. In addition, the number of cells in a radial or axial direction can be modified to allow for a larger or fewer number of cells. Frame 11 can also include a cusp 91. Cusp 91 can be a radiopaque imaging reference to assist in positioning the valve prosthesis 1 in a native valve annulus. Cusp 91 can also assist in anchoring frame 11 in the native valve annulus.

Valve prosthesis 1 also includes a valve 21 that includes individual leaflets that are assembled to the skirt. The leaflets and skirt are formed from a natural or man-made material. Preferred materials for valve 21 include mammalian tissue, such as porcine, equine, or bovine pericardium, or a synthetic or polymeric material. In one aspect of the invention, valve 21 includes three leaflets 31a-c. Adjoining pairs of leaflets are attached to one another to form commissure points 41a-d. Leaflet 31b is attached to leaflet 31a by commissure points 41a and 41d. Leaflet 31b is attached to leaflet 31c by commissure points 41b and 41c. In a preferred embodiment, valve prosthesis 1 is biased to a closed position. Alternatively, valve prosthesis 1 can be biased to an open position. Free edges of leaflets 31b and 31a come together to form coaptation edge 51a, thereby creating a competent seal. Free edges of leaflets 31b and 31c come together to form coaptation edge 51b, thereby creating a competent seal. The length of coaptation edges 51a and 51b can be from approximately 24 mm to approximately 48 mm. In a preferred embodiment, the length of coaptation edges 51a and 51b is approximately 25 mm.

In one aspect of the invention, the contact area between the leaflets at coaptation edges 51a and 51b is minimized to allow for quicker opening and closing of valve leaflets 31a-c. For example, at coaptation edge 51a, approximately 0.5 mm to approximately 6 mm of valve leaflets 31a and 31b touch along the length of coaptation edge 51a. However, the contact area of the leaflets at coaptation edges 51a and 51b is affected by the positioning of valve prosthesis 1 in the native anatomy. In one aspect of the invention, after implantation, valve prosthesis 1 takes approximately 0.06 seconds to open from a closed configuration. Valve prosthesis 1 takes approximately 0.04 seconds to close from an open configuration. Valve prosthesis 1 is also able to operate at approximately 167 ml/second of fluid.

Figure 3:
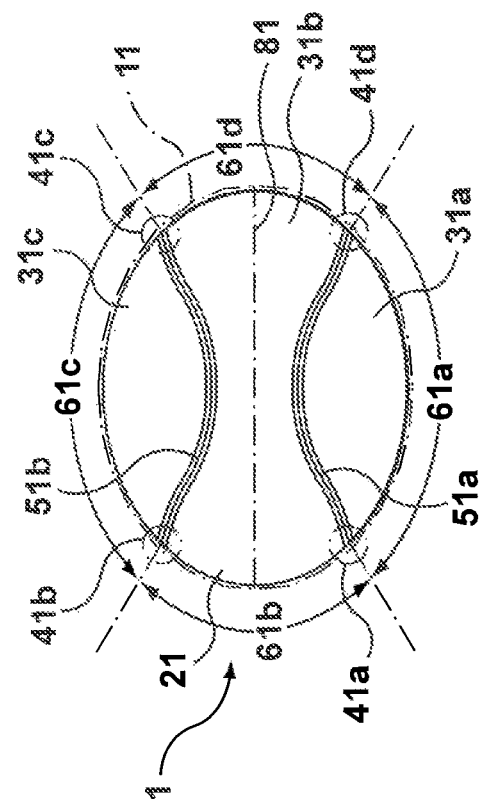
FIG. 3 is a top view of a valve prosthesis.

The bases of leaflets 31a-c are assembled to a skirt 71 and attached to frame 11. Commissure points 41a-d are positioned on frame 11 such that leaflet 31b extends across the center of frame 11, as shown in FIG. 3. Valve prosthesis 1 can include center member 81. In one aspect of the invention, center member 81 attaches to frame 11 between commissure points 41a and 41b and between commissure points 41c and 41d. Center member 81 can be semi-rigid or rigid and can be a suture, nitinol wire, or a synthetic or polymeric material that will not generate a thrombotic response in a patient, or any other material known to a person of ordinary skill in the art. In one aspect of the invention, center member 81 is attached to frame 11 on the outflow side of leaflet 31b. Alternatively, center member 81 can be attached to frame 11 on the inflow side of leaflet 31b. Center member 81 restricts the movement of leaflet 31b and prevents leaflet 31b from collecting blood and parachuting in the outflow direction in the presence of blood flow. As a result, during blood flow, the free edges of leaflet 31b fold along center member 81 and minimize the area of leaflet 31b extending across the orifice area of valve prosthesis 1.

In another aspect of the invention, each commissure point is attached to frame 11 by sewing the commissure point to a cell of frame 11 such that each commissure point occupies an entire cell of frame 11. Alternatively, each commissure point can be attached to frame 11 by sewing the commissure point to a portion of a cell of frame 11. In a preferred embodiment, at least one cell of frame 11 is positioned between commissure points 41a and 41b and commissure points 41c and 41d. Further, at least two cells can be positioned between commissure points 41b and 41c and commissure points 41a and 41d. In one aspect of the invention, commissure points 41a-d are disposed longitudinally offset from coaptation edges 51a-b of the valve body, thereby permitting a smaller delivery profile. Due to the presence of leaflet 31b across the center of frame 11, valve prosthesis 1 may require a delivery system that features an asymmetric member so that the delivery system doesn't interfere with leaflet 31b. Alternatively, a delivery system for valve prosthesis 1 can grasp the outer edge of frame 11 to deliver valve prosthesis 1 into a native valve annulus.

The axial distance from the distal most portion of the base of the valve leaflets to the proximal most portion of the valve leaflets is the leaflet height, h2. The base of the valve leaflets is where the leaflet edges attach to the skirt and the valve frame. In a preferred embodiment, h2 is from approximately 8 mm to approximately 15 mm. The axial distance between the distal and proximal portions of the commissure points is the commissure height, h1. In a preferred embodiment, h1 is approximately 9 mm.

FIG. 3 shows valve 21 in the closed state. Commissure points 41a-d attach to frame 11 and are positioned to form angles 61a-d between the respective commissure points with the center of frame 11 as the vertex of the angles. Angles 61a and 61c can be larger than angles 61b and 61d. In one aspect of the invention, angles 61a and 61c are approximately 170 degrees. In an alternate embodiment, one or more of angles 61a-d can be modified to optimize the function of valve prosthesis 1 by positioning one or more commissure points 41a-d at an alternate portion or cell of frame 11 or by modifying the shape of one or more of leaflets 31a-c. For example, angles 61a and 61c can be between approximately 160 degrees and 180 degrees. Angles 61a and 61c can also be between 90 degrees and 180 degrees. Modifying one or more of angles 61a-d can modify the length of coaptation edges 51a and/or 51b. A longer coaptation edge length correlates to less stress on commissure points 41a-d.

In a further aspect of the invention, leaflets 31a and 31c are approximately the same size. Alternatively, leaflets 31a and 31c can be different sizes. Modifying the sizes of leaflets 31a and 31c can also affect angles 61a-d. For example, if leaflets 31a and 31c are different sizes, angle 61c can be larger than angle 61a, or vice versa.

The configuration involving four commissure points can increase the coaptation length of the valve leaflets. As a result, the four commissure points experience less deflection than a valve having three commissure points. This allows the leaflets to maintain a rapid opening and closing time. The four commissure design also enables the valve prosthesis to maintain reliability with a low commissure height. The low commissure height allows valve prosthesis 1 to replace the native mitral valve. Furthermore, a low commissure height correlates to a valve prosthesis that is shorter in the axial direction that is easier to position and align in a native valve annulus. The four commissure points also enable the valve to maintain hemodynamic performance in a severely elliptical configuration by mitigating impact in the coaptive region. This configuration also provides a more uniform distribution of stresses along coaptation edges 51a-b of leaflets 31a-c allowing valve prosthesis 1 to exhibit greater reliability and a longer operating life than current catheter delivered valve prostheses.

Figure 4:
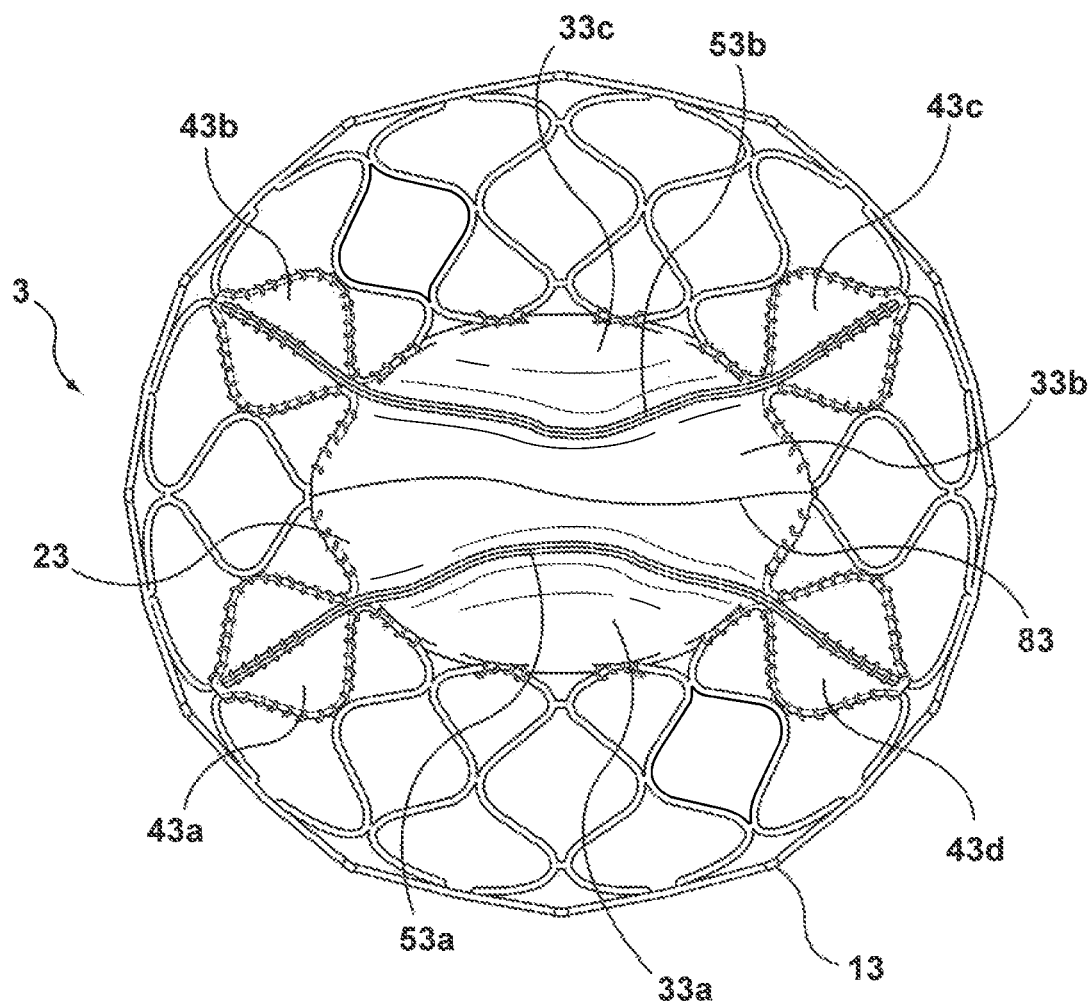
FIG. 4 is a top view of a valve prosthesis according to an alternate aspect of this disclosure.

In an alternate aspect of the invention shown in FIG. 4, from a side view, frame 13 is an hourglass shape where the outflow portion flares out such that the diameter of the outflow portion of the frame is larger than the diameter of the inflow portion of the frame. In one aspect of the invention, commissure points 43a-d are angled outward from the center of frame 13. In this configuration, the most proximal portions of commissure points 43a-d are further from the center of frame 13 than the distal portions of commissure points 43a-d. In an alternate embodiment, the commissure points can be angled inward towards the center of the frame. The commissure points can also be oriented vertically on the frame, as shown in FIG. 3.

Figure 5:
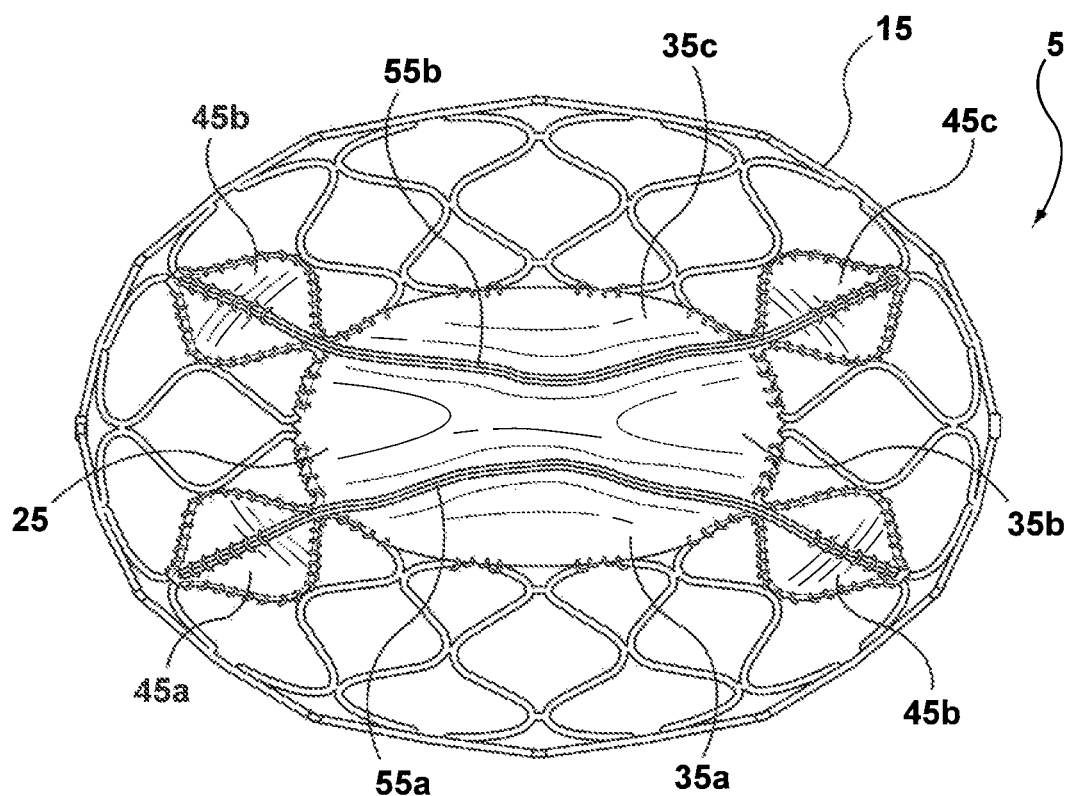
FIG. 5 is a top view of a valve prosthesis according to an alternate aspect of this disclosure.
Figure 6:
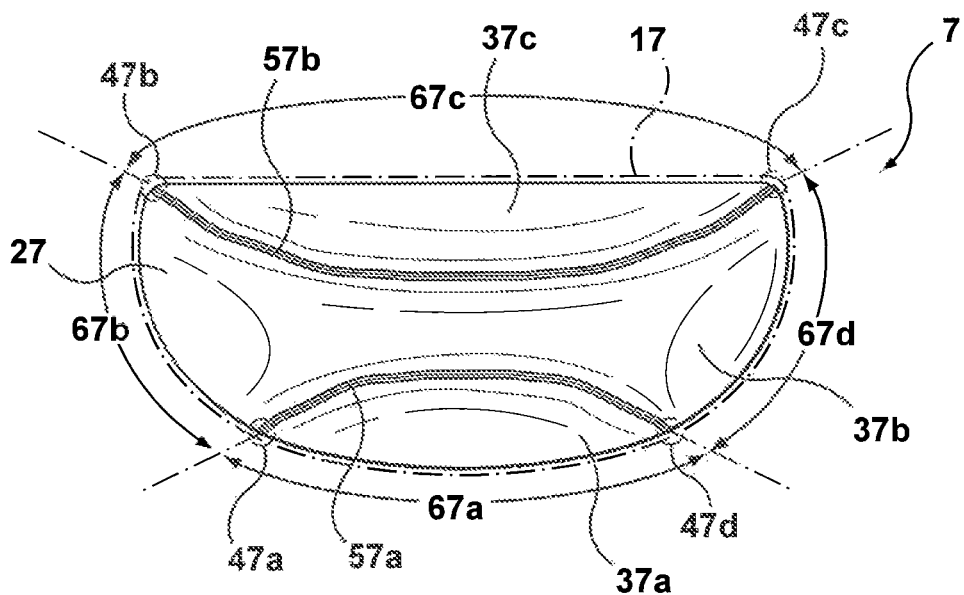
FIG. 6 is a top view of a valve prosthesis according to an alternate aspect of this disclosure.

FIGS. 5-6 are top views of alternative aspects of the invention showing alternate frame shapes. In FIG. 5, from a top view, the frame is an elliptical shape. In this embodiment, leaflets 35a and 35c have approximately the same size and area and angles 65a and 65c are approximately equal. In a preferred embodiment, angles 65a and 65c are approximately 170 degrees. Furthermore, coaptation edges 55a and 55b are approximately equal in length. Similar to valve prosthesis 1 discussed in FIGS. 1-3, the size and area of leaflets 35a-c can be modified so that leaflets 35a and 35c do not have approximately the same size. The placement of commissure points 45a-d on frame 15 can also be modified to alter angles 65a-d in order to optimize the function of valve prosthesis 5.

In FIG. 6, from a top view, frame 17 is D-Shaped. In this aspect of the invention, leaflet 37c can have a larger area than leaflet 37a and corresponding angle 67c can be greater than angle 67a. As a result, coaptation edge 57b can have a greater length than coaptation edge 57a. Alternatively, leaflet 37a can be larger than leaflets 37c and corresponding angle 67a can be larger than angle 67c. In a preferred embodiment, angle 67c is approximately 170 degrees. In alternate aspects of the invention, the sizes of leaflets 37a-c and the angles 67a-d can be modified in order to optimize the function of valve prosthesis 7.

Figure 7:
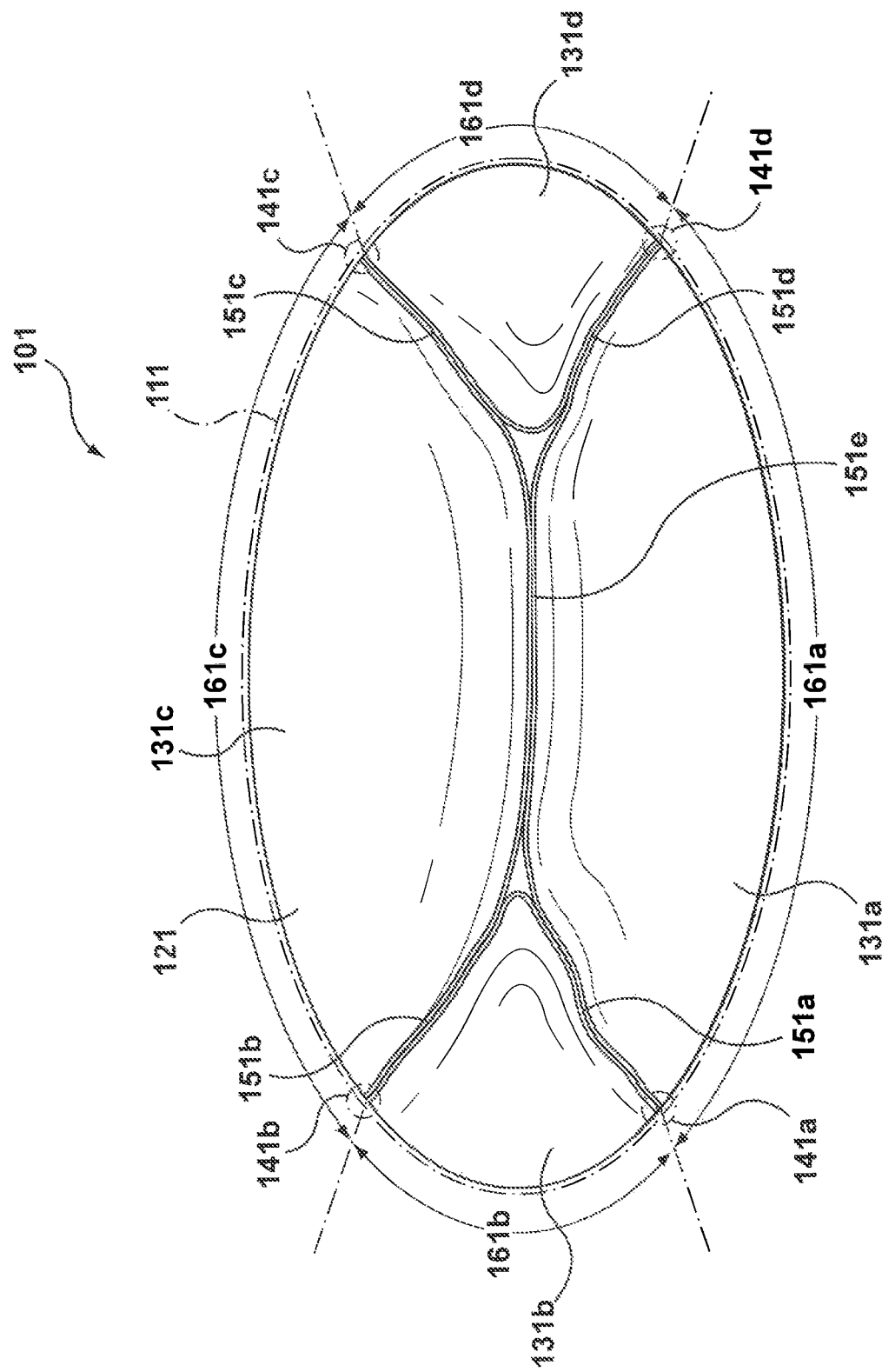
FIG. 7 is a top view of a valve prosthesis according to an alternate aspect of this disclosure.

FIG. 7 shows an alternate valve prosthesis 101 having four leaflets 131a-d and four commissure points 141a-d. Leaflets 131a and 131c are approximately the same size having approximately the same area. In an alternate aspect of the invention, leaflets 131a and 131c can be different sizes. Leaflet 131a is attached to leaflet 131b at commissure point 141a and to leaflet 131d at commissure point 141d. Leaflet 131c is attached to leaflet 131b at commissure point 141b and to leaflet 131d at commissure point 141c. Free edges of leaflets 131a and 131b come together to form coaptation edge 151a. Free edges of leaflets 131b and 131c come together to form coaptation edge 151b. Free edges of leaflets 131c and 131d come together to form coaptation edge 151c. Free edges of leaflets 131d and 131a come together to form coaptation edge 151d. Free edges of leaflets 131a and 131c come together to form coaptation edge 151e. Coaptation edges 151a-e thereby create a competent seal. In a preferred embodiment, the length of coaptation edge 151e is larger than the length of any of coaptation edges 151a-d.

Leaflets 131a-d are assembled to a skirt (not shown), similar to valve prosthesis 1. Commissure points 141a-d are attached to frame 111 which is elliptical from a top view. Commissure points 141a-d are arranged to form angles 161a-161d, where the center of frame 111 is the vertex of the angles. Frame 111 can be any other shape known to a person of ordinary skill, including but not limited to circular, or D shaped from a top view, or tapered, conical, or cylindrical from a side view. In one aspect of the invention, angles 161a and 161c are larger than angles 161b and 161d. In a preferred embodiment, angles 161a and 161c are approximately 170 degrees. In an alternate embodiment, one or more of angles 161a-d can be modified to optimize the function of valve prosthesis 101 by positioning one or more commissure points 141a-d on an alternate portion of frame 111 or by modifying the shape or area of one or more of leaflets 131a-d. Modifying one or more of angles 161a-d can modify the length of coaptation edges 151a-e.

Figure 8:
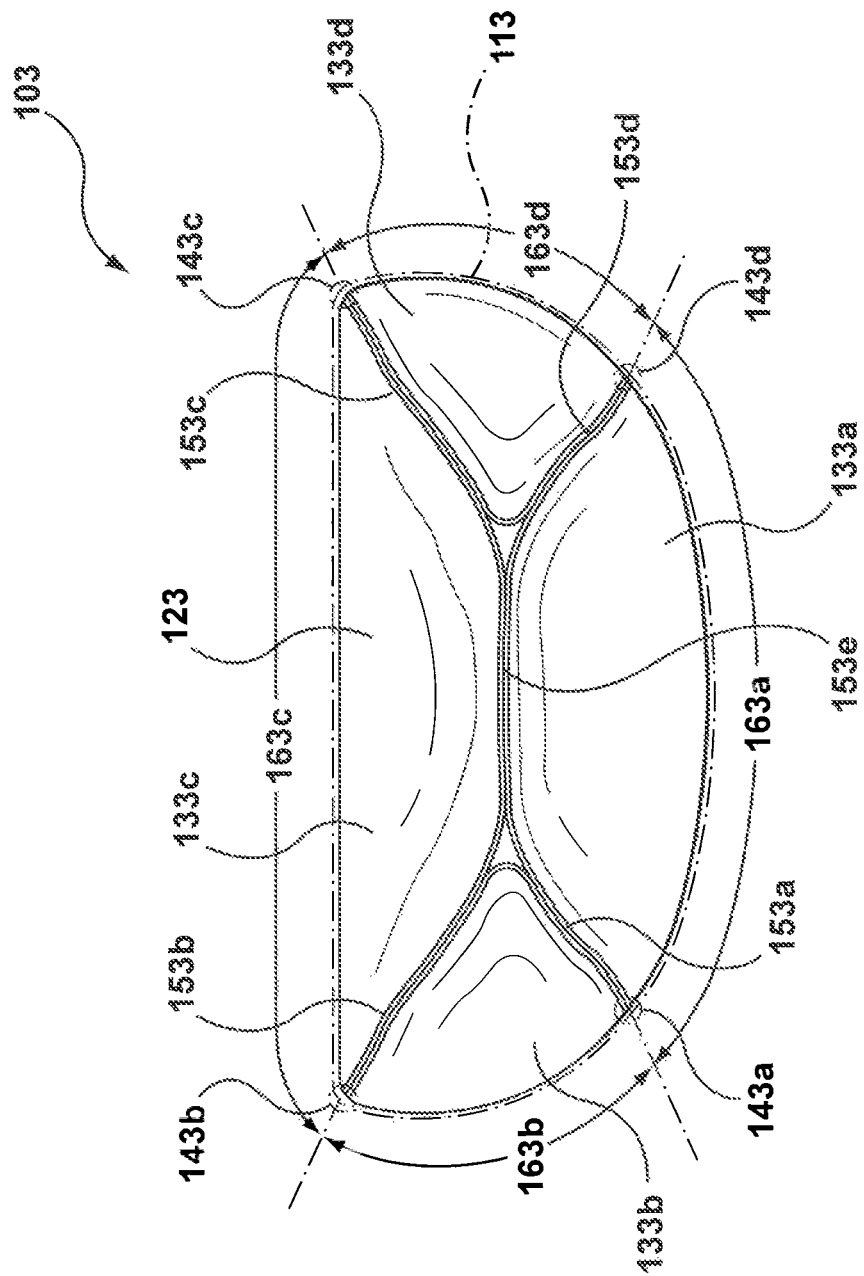
FIG. 8 is a top view of a valve prosthesis according to an alternate aspect of this disclosure.

In an alternate aspect of the invention shown in FIG. 8, from a top view, frame 113 is D-Shaped. In this aspect of the invention, leaflet 133c has a larger area than leaflet 133a and corresponding angle 163c is greater than angle 163a. Furthermore, leaflet 133a is larger than leaflets 133b and 133d and corresponding angle 163a can be larger than angles 163b and 163d. In a preferred embodiment, angle 163c can be 170 degrees. In alternate aspects of the invention, the sizes of leaflets 37a-c and the angles 67a-d can be modified to optimize the function of valve prosthesis 103. Similar to valve prosthesis 101 discussed above with respect to FIG. 7, leaflets 133a-d come together to form coaptation edges 153a-e. In a preferred embodiment, the length of coaptation edge 153e is greater than the length of any of coaptation edges 153a-d.

The valve prosthesis can replace the function of a tricuspid or bicuspid heart valve including the mitral valve, the aortic valve, the pulmonary valve, or the tricuspid valve. The valve can be delivered, for example, transeptally, transapically, transradially, or transatrially.

Implantation of the valve prosthesis will now be described. As discussed above, the valve prosthesis preferably comprises a self-expanding frame that can be compressed to a contracted delivery configuration onto an inner member of a delivery catheter. The valve prosthesis and inner member can then be loaded into a delivery sheath of conventional design, e.g., having a diameter of less than 20-24 French. Due in part to the fact that the commissure points are longitudinally offset from the coaptation edges of the leaflets, and due to the ability to maintain a lower commissure height, it is expected that the valve prosthesis can achieve a significantly smaller delivery profile than previously-known percutaneously-deliverable replacement valves.

The delivery catheter and valve prosthesis are then advanced in a retrograde manner through the femoral artery and into the patient's descending aorta. The catheter then is advanced, under fluoroscopic guidance, over the aortic arch, through the ascending aorta and mid-way across the defective aortic valve. Once positioning of the catheter is confirmed, the sheath of the delivery catheter can be withdrawn proximally, thereby permitting the valve prosthesis to self-expand.

As the valve prosthesis expands, it traps the leaflets of the patient's defective aortic valve against the valve annulus, retaining the native valve in a permanently open state. The outflow section of the valve prosthesis expands against and aligns the prosthesis within the ascending aorta, while the inflow section becomes anchored in the aortic annulus of the left ventricle, so that the skirt reduces the risk of perivalvular leaks.

Alternatively, the valve prosthesis can be delivered through a transapical procedure. In a transapical procedure, a trocar or overtube is inserted into the left ventricle through an incision created in the apex of a patient's heart. A dilator is used to aid in the insertion of the trocar. In this approach, the native valve (e.g. the mitral valve) is approached from the downstream relative to the blood flow. The trocar is retracted sufficiently to release the self-expanding valve prosthesis. The dilator is preferably presented between the valve leaflets. The trocar can be rotated and adjusted as necessary to properly align the valve prosthesis. The dilator is advanced into the left atrium to begin disengaging the proximal section of the valve prosthesis from the dilator.

In an alternate aspect of the invention, the valve prosthesis can be delivered through a transatrial procedure. In this procedure, the dilator and trocar are inserted through an incision made in the wall of the left atrium of the heart. The dilator and trocar are advanced through the native valve and into the left ventricle of heart. The dilator is then withdrawn from the trocar. A guide wire is advanced through the trocar to the point where the valve prosthesis comes to the end of the trocar. The valve prosthesis is advanced sufficiently to release the self-expanding frame from the trocar. The trocar can be rotated and adjusted as necessary to properly align the valve prosthesis. The trocar is completely withdrawn from the heart such that the valve prosthesis self-expands into position and assumes the function of the native valve.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A valve prosthesis comprising:
a valve body; and
a self-expanding frame,
wherein the valve body includes a first leaflet, a second leaflet, and a third leaflet, wherein the second leaflet extends between the first leaflet and the third leaflet such that the first and third leaflets are separated from each other by the second leaflet and wherein the first and second leaflets are sewn together to form a first commissure point and a second commissure point, and the second and third leaflets are sewn together to form a third commissure point and a fourth commissure point, and wherein the four commissure points are sewn to the frame.

2. The valve prosthesis according to claim 1, wherein a first angle is formed between the first commissure point and the second commissure point with a vertex of the first angle being a center of the frame, a second angle is formed between the second commissure point and the third commissure point with a vertex of the second angle being the center of the frame, a third angle is formed between the third commissure point and the fourth commissure point with a vertex of the third angle being the center of the frame, and a fourth angle is formed between the fourth commissure point and the first commissure point with a vertex of the fourth angle being the center of the frame such that the center of the frame is the vertex of each of the first, second, third and fourth angles, and wherein the first angle and the third angle are greater than the second angle and the fourth angle.

3. The valve prosthesis according to claim 2, wherein the first angle and the third angle are approximately equal.

4. The valve prosthesis according to claim 2, wherein the first angle and the third angle are approximately 170 degrees.

5. The valve prosthesis according to claim 2, wherein the first angle is greater than the third angle.

6. The valve prosthesis according to claim 2, wherein the second angle and the fourth angle are approximately equal.

7. The valve prosthesis according to claim 1, wherein a free edge of the first leaflet and a first free edge of the second leaflet form a first coaptive edge between the first commissure point and the second commissure point, and wherein a second free edge of the second leaflet and a free edge of the third leaflet form a second coaptive edge between the third commissure point and the fourth commissure point.

8. The valve prosthesis according to claim 7, wherein the first coaptive edge is approximately equal in length to the second coaptive edge.

9. The valve prosthesis according to claim 7, wherein the second coaptive edge is greater in length than the first coaptive edge.

10. The valve prosthesis according to claim 1, wherein the second leaflet extends across a center of the frame.

11. The valve prosthesis according to claim 10, further comprising:
a center member attached to the frame that extends across the second leaflet.

12. The valve prosthesis according to claim 11, wherein the center member is disposed on an outflow side of the second leaflet and is configured to restrict movement of the second leaflet in the presence of blood flow through the valve prosthesis.

13. The valve prosthesis according to claim 11, wherein a first end of the center member is attached to the frame between the first commissure point and the fourth commissure point and a second end of the center member is attached to the frame between the second commissure point and the third commissure point.

14. A method of treating a valve disorder in a patient's heart, comprising:
loading a valve prosthesis onto a delivery system;
advancing the delivery system and valve prosthesis through an incision into the patient's vasculature and into the patient's heart;
releasing the valve prosthesis from the delivery system; and
withdrawing the delivery system from the patient's heart,
wherein the valve prosthesis includes:
a valve body; and
a self-expanding frame,
wherein the valve body includes a first leaflet, a second leaflet, and a third leaflet, wherein the second leaflet extends between the first leaflet and the third leaflet such that the first and third leaflets are separated from each other by the second leaflet and wherein the first and second leaflets are sewn together to form a first commissure point and a second commissure point, and the second and third leaflets are sewn together to form a third commissure point and a fourth commissure point, and wherein the four commissure points are sewn to the frame.

* * * * *